United States Patent [19]
De Haen et al.

[11] Patent Number: 6,007,808
[45] Date of Patent: Dec. 28, 1999

[54] PHARMACEUTICAL AND DIET FORMULATIONS FOR THE PROPHYLAXIS AND TREATMENT OF GASTROINTESTINAL DISORDERS

[75] Inventors: Christoph De Haen; Luigia Gozzini, both of Milan, Italy

[73] Assignee: Dibra S.p.A., Milan, Italy

[21] Appl. No.: 08/973,676

[22] PCT Filed: Jun. 19, 1996

[86] PCT No.: PCT/EP96/02650

§ 371 Date: Dec. 12, 1997

§ 102(e) Date: Dec. 12, 1997

[87] PCT Pub. No.: WO97/00688

PCT Pub. Date: Jan. 9, 1997

[30] Foreign Application Priority Data

Jun. 23, 1995 [IT] Italy ................................. MI95A1359

[51] Int. Cl.⁶ .................................................. C12N 1/20
[52] U.S. Cl. .................... 424/93.4; 424/93.3; 424/93.45; 424/93.48; 514/561
[58] Field of Search .................. 424/93.4, 93.3, 424/93.45, 93.48, 195.1, 520; 514/561

[56] References Cited

U.S. PATENT DOCUMENTS 5,397,803 3/1995 Smith et al. ............................. 514/563
5,738,651 4/1998 Walton et al. ............................ 604/83

FOREIGN PATENT DOCUMENTS 0 199 535  10/1986  European Pat. Off. .
03067046   10/1991  Japan .

OTHER PUBLICATIONS

Bengmark, S. et al., "Gastrointestinal Surface Protection and Mucosa Reconditioning", Journal of Parenteral and Enteral Nutrition, vol. 19, No. 5, 1995, pp. 410–415.

Helwig, H. et al., "Helwig/Otto Arzneimittel", Ein Handbuch für Ärzte und Apotheker, Oct. 1988, pp. 38–92.

Lewenstein, A. et al., "Biological Properties of SF 68, A New Approach . . . ", Current Therapeutic Research, Clinical and Experimental, vol. 26, No. 6, Section 2, Dec. 1979, pp. 967–981.

*Primary Examiner*—Jean C. Witz
*Attorney, Agent, or Firm*—Nixon & Vanderhye P.C.

[57] ABSTRACT

The present invention refers to pharmaceutical and diet formulations for the prophylaxis and treatment of gastrointestinal disorders.

23 Claims, No Drawings

PHARMACEUTICAL AND DIET FORMULATIONS FOR THE PROPHYLAXIS AND TREATMENT OF GASTROINTESTINAL DISORDERS

The present invention refers to pharmaceutical and dietary formulations for the prophylaxis and treatment of gastrointestinal disorders.

BACKGROUND OF THE INVENTION

Gastrointestinal disorders, including viral, bacterial and protozoal infections, as well as chronic inflammatory diseases, or radiation damages, exert a stress on gastrointestinal cells. The main nutrient of mucosal cells of the gastrointestinal tract is glutamine. This amino acid, usually non-essential, becomes "conditionally essential" in pathologies characterized by a glutamine requirement that exceeds the individual's ability to produce sufficient amount of this amino acid. Enteral or parenteral administration of glutamine improves nutritional management and recovery of the patients (Castel L M et al. (1994) Amino Acids 7, 231–243; Lacey J M, Wilmore D W (1990) Nutr. Rev. 48 (8), 297–309). Glutamine, apart from being the preferred fuel for cells with a rapid proliferation rate such as enterocytes and lymphocytes, is also a regulator for acid-base balance through the production of ammonia. Enterocytes are the most important cells of small intestine which use glutamine as an energy source (Wu G et al. (1995) Am. J. Physiol. 266, R334–R342; Nagy L E, Kretchmer N (1988) J. Nutr. 118 (2), 189–193). As a matter of fact, intestinal cells absorb a remarkable amount of glutamine supplied with the diet and whenever the supply of this amino acid is decreased, the amino acid is taken up from the blood. Low levels of glutamine, experimentally induced in animals, for instance through glutaminase administration, cause intestinal disorders, e.g. chronic diarrhoea, villous atrophy, etc., (Castel L M et al. (1994) Amino Acids 7, 231–243) thus confirming the importance of glutamine for the intestine. In conclusion, glutamine can be insufficient in certain disorders of the gastrointestinal tract. In such situations of glutamine deficiency, the gastrointestinal cells are more vulnerable and therefore more exposed to injury caused, for instance, by infectious agents or ionizing radiations. Conversely injury and stress to gastrointestinal cells can augment their energetic needs, and thus their requirement of glutamine for survival or replacement. Consequently glutamine administration can augment the ability of gastrointestinal cells to withstand injury. In addition, the above mentioned positive effects on gastrointestinal cells due to glutamine administration can be further enhanced by the addition of arginine which acts both on the immune system and the wound-healing rate (Wu G et al. (1995) Am. J. Physiol. 266, R334–R342). Carbohydrates are thought to act in synergy with glutamine, but alone they cannot substitute it (Wu G et al. (1995) Am. J. Physiol. 266, R334–R342).

In solution glutamine is not completely stable. In particular, during heat sterilization of glutamine solutions, pyroglutamate and glutamic acid may form. Glutamine containing polypeptides are much more stable. Upon ingestion of such polypeptides, glutamine may be released in the stomach and intestine by proteases. Therefore a sufficient amount of glutamine can be also achieved by administering small or large polypeptides containing glutamine such as for instance L-alanyl-L-glutamine or glycyl-L-glutamine or glycyl-glycyl-L-glutamine.

Lactic acid bacteria, particularly lactobacilli, as well as other bacteria isolated from the gastrointestinal tract of healthy human beings or animals, have long been known to produce a prophylactic and therapeutic effect on gastrointestinal infections (Zoppi G. et al.(1982) Eur. J. Pediatrics 139, 18–21). Such bacteria go under the name of eubiotic bacteria. Some bacterial species may compete with pathogenic ones for nutrients and/or attachment sites on the gastrointestinal mucous membrane. In addition they can favor the return of pH to normal values. For instance, the strain *Enterococcus faecium* SF 68 (earlier called *Streptococcus faecium* SF 68), originally isolated from pig intestines, has been proven to be effective in clinical studies (Borgia M et al. (1982) Curr. Ther. Res. 31(2), 265–271; Bellomo G et al. (1980) Curr. Ther. Res. 28(6), 927–936; Camarri E et al. (1981) Chemotherapy 27, 466–470; Wunderlich P F et al. (1989) J. Int. Med. Res. 17, 333–338). Due to a low affinity of this bacterium for the gastrointestinal mucous membrane, a regular administration for a prolonged period is needed. In contrast, patients treated with bacteria showing good adherence to the mucous membrane, will require less frequent and less prolonged administration to achieve a cure.

Bacteria belonging to the Lactobacills genus, which are able to adhere to human gastrointestinal mucous membranes, and thus competing with pathogens with similar adhering properties, have been isolated from healthy human beings and their characteristics are disclosed in U.S. Pat. No. 4,839,281, U.S. Pat. No. 5,032,399, and WO Patent Applications 95/33046. For instance, U.S. Pat. Nos. 4,839,281 and 5,032,399 disclose the *Lactobacillus acidophilus* strain ATCC 53103 isolated from adults and characterized by good adhesion properties. The taxonomic classification of the strain was more recently revised and the strain classified as *Lactobacillus casei* sbsp. *rhamnosus*. In certain countries dietary products based on this strain, commonly called Lactobacillus GG, have reached the market (e.g., Gefilus$^{(R)}$ fermented milk and Gefilus$^{(R)}$ fermented whey drink in Finland). Other strains, with dramatically improved adhesion properties, belonging to the genus Lactobacillus are the strains CNCM I-1390, CNCM I-1391, CNCM I-1392, and CNCM I-1447. They are disclosed in WO Patent Applications 95/33046. In addition to excellent adhesion properties they are characterized by favourable technological properties with respect to production and conservation.

Antibiotics are widely used to treat acute infections. The gastrointestinal flora become impoverished. Lactobacilli administration may be used to restore a well functioning flora. In such cases it could be useful to select bacteria which are resistant to antibiotics. As a matter of fact, many bacteria show an intrinsic resistance to antibiotics. Otherwise, antibiotic resistance can be induced by mutagenesis, for example by using agents which speed up the normal mutation rate. Then, the mutated strains are selected by well-known procedures. Alternatively, widely known techniques of genetic engineering can produce bacteria endowed with specific resistance to antibiotics.

Some eubiotic bacteria show a bacteriostatic or even bactericidal behavior toward pathogens. These activities partially result from the production of metabolites, such as lactic acid, acetic acid, and hydrogen peroxide, which make the environment less favorable for the growth of pathogens. In addition, several lactic acid bacteria are known to produce other substances such as antibiotics and bacteriocins. And obviously these bacteria gather special interest.

DESCRIPTION OF THE INVENTION

In order to verify whether the simultaneous presence of glutamine could possibly influence the growth of eubiotic bacteria, in vitro experiments were performed. Eubiotic strains were incubated at 37° C. under 5% $CO_2$ atmosphere in MRS broth (lactobacilli strains) or BHI broth (*Enterococcus faecium*) both in the absence and in the presence of 4% glutamine. Bacterial counts were carried out after 12 h, 24 h and 48 h. The results are summarized in Table I.

TABLE I

Bacterial growth in the absence and in the presence of glutamine at different times[a]

| Strains | 12 h | | 24 h | | 48 h | |
| --- | --- | --- | --- | --- | --- | --- |
| | −Gln | +Gln | −Gln | +Gln | −Gln | +Gln |
| ATCC 53103 | 9.1 | 9.0 | 9.4 | 9.3 | 9.0 | 9.2 |
| CNCM I-1447 | 9.0 | 8.8 | 9.0 | 8.6 | 9.1 | 8.9 |
| CNCM I-1391 | 9.9 | 8.9 | 9.2 | 9.1 | 9.5 | 9.5 |
| Enterococcus faecium | 8.4 | 8.5 | 9.5 | 9.3 | 9.0 | 9.4 |

[a]Values are expressed as log CFU/mL. CFU = Colony Forming Unit.

The data indicate that the simultaneous presence in culture medium of glutamine does not inhibit the growth of bacteria. Similar experiments were carried out in the presence of bile as well as at different values of pH. Even in these tests the presence of glutamine did not interfere with the growth of the tested bacteria.

As part of the present invention, it has now been found that thanks to the combination of therapeutic bacteria and glutamine or glutamine containing polypeptides, highly advanced pharmaceutical products can be manufactured, showing surprisingly favorable therapeutic effects over each components of the combination taken alone. In particular indications were obtained that therapy with eubiotic bacteria accelerates recovery.

In pharmaceutical formulations, eubiotic bacteria are usually lyophilized to preserve their stability as disclosed in U.S. Pat. No. 3,897,307 and in European Patent Appl. EP-A-259739. In some cases, bacteria lyophilization requires the use of stabilizers in the aqueous phase to reduce the formation of long ice crystals. Said agents include, for instance, carbohydrates, amino acids, polypeptides, proteins, synthetic polymers and dimethylsulfoxide. U.S. Pat. No. 3,897,307 discloses the preparation of stabilized dried bacterial strains, by adding, before drying, "potentiators", in particular L-ascorbic acid and water-soluble edible salts to the grown culture. Another compound which can be used in this process is trehalose.

It has now surprisingly been found that glutamine or polypeptides containing glutamine, in particular in the presence of added carbohydrates, and/or other complex mixtures of extracts of animal or vegetal origin, such as, for example, yeast or meat extracts or dry milk, can also be used to stabilize bacteria during lyophilization. Alternatively, during lyophilization bacteria can be stabilized by any usual method known to the skilled technician and stored in the form of a granulate mixture containing the other components of the pharmaceutical product, that's to say glutamine or a derivative thereof preferably together with additives such as arginine or carbohydrates or dry milk and so on. Experimental lyophylization tests, conducted on eubiotic bacteria alone and in the presence of 4% glutamine, or a mixture of glutamine and dry milk, confirmed the above statement. Alternatively, lyophilized bacteria with its additives and glutamine or glutamine-containing polypeptides and its additives be stored in separate sachets to be ingested in synchrony after dissolution or suspension of each of the two components of the pharmaceutical product in water.

Presently some bacterial products are lyophilized owders in pharmaceutical capsules. Obviously one particular realization of the present invention envisions the preparation of said bacteria containing capsules which are to be ingested with a drink prepared by dissolving/suspending the other components, glutamine or glutamine-containing polypeptides plus eventual additives such as arginine in water. In this case, the capsules and the sachets containing the amino acids can be packaged together in a single confection assuring a correct single-dose administration of the two different components.

EXAMPLE 1

Capsules containing $10^6$–$10^{12}$ cells of lyophilized *Enterococcus faecium* SF 68 are packaged in blisters. Sachets, in number equal to capsules, containing a granulate of 3 g of glutamine and 6 g of sucrose are packaged together with the blister. To prepare a single dose, the content of the sachet must be dissolved/suspended in 100–150 mL of water, and then one capsule must be swallowed with help of the prepared solution/suspension, and if necessary, of additional water.

EXAMPLE 2

The strain *Lactobacillus casei* sbsp casei CNCM I-1391 is grown in MRS broth and the cells harvested by centrifugation. The cells are resuspended at a concentration of approximately $10^{10}$ cells/mL in a filter sterilized solution consisting of 75 g/L of L-glutamine and 150 g/L of sucrose and then lyophilized. The resulting lyophilized product is distributed in 9 g doses into sealed sachets. Each dose consists of the content of one sachet dissolved/suspended in 100–150 mL of water.

EXAMPLE 3

A formulation similar to that of Example 2 was obtained by using a mixture of lactobacilli strains CNCH I-1390 and CNCH 1–1447 at a concentration of approximately $10^9$ cells/mL for each strain.

EXAMPLE 4

Sachets containing a granulate consisting of a mixture of 3 g of glutamine, 6 g of sucrose, and at least $10^7$ *Lactobacillus acidophilus* CNCM I-1447, are prepared. The formulation is administered after diluting the content sachet in 100–150 mL of water.

EXAMPLE 5

The formulation of Example 4 was prepared with strain ATCC 53103 at the same concentration.

EXAMPLE 6

Sachets containing a granulate consisting of 4 g of glycyl-glycyl-L-glutamine, 3 g of L-arginine and 5 g of glucose and sachets containing at least $10^6$ *Lactobacillus casei* sbsp *casei* strain CNCM I-1391, in a dextran stabilized lyophilized form, are prepared. The content of each kind of the sachets should be dissolved/suspended in 100–150 mL of water to obtain the desired therapeutical, prophylactic or dietetical dose.

EXAMPLE 7

Two patient volunteers showing already for two days the typical symptoms of traveller's diarrhoea consumed on the third and fourth day, in the morning, at noon and in the evening a capsule containing *Streptococcus faecium* SF 68 (Bioflorin$^{(R)}$, Bracco S.p.A., Milan) together with a 3 g dose of glutamine and 6 g sucrose. There was observed a rapid sense of relief and no return of symptoms when after two days the therapy was stopped.

The deposits referred to above by the initials CNCM followed by an accession number were deposited under the terms of the Budapest Treaty by the assignee of this application at the Collection Nationale de Cultares de Microorganismes (CNCM) at Institute Pasteur, 25 Rue du Docteur Roux, 75724 Paris CEDEX 15, France and are summarized as follows:

| Accession No. CNCM- | Depositor's Ref. | Date Deposited |
|---|---|---|
| 1-1447 | B21190 | July 13, 1994 |
| 1-1392 | B21080 | January 13, 1994 |
| 1-1391 | B21070 | January 13, 1994 |
| 1-1390 | B21060 | January 13, 1994 |

We claim:

1. A pharmaceutical or dietary composition consisting essentially of at least one strain of a eubiotic bacteria in an amount of from $10^6$ to $10^{12}$ bacterial cells per dose together with glutamine in an amount of from 0.5 to 10 grams per dose or an equivalent amount of a glutamine-containing polypeptide, and optionally a pharmaceutical stabilizer or carrier.

2. The composition of claim 1 further containing L-arginine in an amount of from 0.5 to 10 grams per dose.

3. The composition of claim 1 further containing a carbohydrate.

4. The composition of claim 1 further containing from 0.5 to 10 grams of an animal or vegetable extract.

5. The composition of claim 1 containing $10^8$ to $10^{11}$ bacterial cells per dose.

6. The composition of claim 1 containing from 2 to 5 grams of glutamine or equivalent amount of glutamine-containing polypeptide.

7. The composition of claim 1 in which at least one component is lyophilized.

8. The composition of claim 1 in which the lyophilized component is stabilized.

9. The composition of claim 8, in which the stabilizer is selected from glutamine, glutamine-containing polypeptides, amino acids and carbohydrates.

10. The composition of claim 7, in which the bacteria cells are lyophilized.

11. The composition of claim 10, in which said lyophilized bacteria, optionally stabilized, are mixed with a granulate containing the other components.

12. The composition of claim 10, in which the lyophilized bacteria are packaged separately from the other components, the two packages constituting the dose of the pharmaceutical product.

13. The composition of claim 1, in which the bacteria are lactic acid bacteria.

14. The composition of claim 13, in which the bacteria are lactobacilli.

15. The composition of claim 13, in which the bacteria are lactobacilli capable of adhering to the intestinal mucous membrane.

16. The composition of claim 14, in which the lactobacilli are of human origin isolated from the gastrointestinal tract of healthy humans.

17. The composition of claim 14 wherein the lactobacilli is selected from a strain selected from accession numbers CNCM 1-1447, CNCM 1-1392, CNCM 1-1391 and CNCM 1-1390.

18. A method of treating gastrointestinal disorders by providing glutamine to the gastrointestinal cells, said method comprising administering to a subject in need of same a composition consisting essentially of at least one strain of a eubiotic bacteria in an amount of from $10^6$ to $10^{12}$ bacterial cells per dose together with glutamine in an amount of from 0.5 to 10 grams per dose or an equivalent amount of a glutamine-containing polypeptide the composition also optionally including a pharmaceutical stabilizer or carrier.

19. The method of claim 18 in which the composition further contains L-arginine in an amount of from 0.5 to 10 grams per dose.

20. The method of claim 18 in which the composition further contains a carbohydrate.

21. The method of claim 18 in which the composition further contains from 0.5 to 10 grams of an animal or vegetable extract.

22. The method of claim 18 in which the composition further contains $10^8$ to $10^{11}$ bacterial cells per dose.

23. A method of treating diarrhea by providing glutamine to the gastrointestinal cells, said method comprising administering to a subject in need of same a composition consisting essentially of at least one strain of a eubiotic bacteria in an amount of from $10^6$ to $10^{12}$ bacterial cells per dose together with glutamine in an amount of from 0.5 to 10 grams per dose or an equivalent amount of a glutamine-containing polypeptide, the composition also optionally including a pharmaceutical stabilizer or carrier.

* * * * *